United States Patent
Park et al.

(10) Patent No.: US 10,562,265 B2
(45) Date of Patent: Feb. 18, 2020

(54) METHOD FOR MEASURING PEELING STABILITY OF RELEASE FILM AND RELEASE FILM LAMINATE

(71) Applicant: LG Chem, Ltd., Seoul (KR)

(72) Inventors: Jun-Hyoung Park, Gyeonggi-do (KR); Jang-Soon Kim, Gyeonggi-do (KR)

(73) Assignee: LG Chem, Ltd. (KR)

(*) Notice: Subject to any disclaimer, the term of this patent is extended or adjusted under 35 U.S.C. 154(b) by 260 days.

(21) Appl. No.: 15/522,204

(22) PCT Filed: Oct. 26, 2015

(86) PCT No.: PCT/KR2015/011340
§ 371 (c)(1),
(2) Date: Apr. 26, 2017

(87) PCT Pub. No.: WO2016/068559
PCT Pub. Date: May 6, 2016

(65) Prior Publication Data
US 2017/0313025 A1    Nov. 2, 2017

(30) Foreign Application Priority Data
Oct. 28, 2014 (KR) .......................... 10-2014-0147318

(51) Int. Cl.
*G01N 19/04* (2006.01)
*B32B 7/06* (2019.01)
(Continued)

(52) U.S. Cl.
CPC ............... *B32B 7/06* (2013.01); *B32B 5/022* (2013.01); *B32B 5/24* (2013.01); *B32B 5/26* (2013.01);
(Continued)

(58) Field of Classification Search
CPC .. B32B 7/06; B32B 7/12; B32B 27/00; B32B 27/06; B32B 37/12; B32B 37/26;
(Continued)

(56) References Cited

U.S. PATENT DOCUMENTS

2014/0127437 A1* 5/2014 Malfait ............... B32B 7/06 428/36.7
2014/0363628 A1* 12/2014 Nakai ................. B32B 7/06 428/141
(Continued)

FOREIGN PATENT DOCUMENTS

CN 103857761 A 6/2014
JP 1989301781 5/1989
(Continued)

OTHER PUBLICATIONS

International Search Report from PCT/KR2015/011340, dated Feb. 5, 2016.
(Continued)

*Primary Examiner* — Max H Noori
(74) *Attorney, Agent, or Firm* — Lerner, David, Littenberg, Krumholz & Mentlik, LLP

(57) ABSTRACT

Provided is a method for measuring the peeling stability of a release film and a release film laminate by measuring a high-speed release strength balance and a low-speed strength balance on the basis of General Formulas 1 and 2.

7 Claims, 1 Drawing Sheet

(51) Int. Cl.
| | |
|---|---|
| B32B 7/12 | (2006.01) |
| B32B 27/32 | (2006.01) |
| B32B 29/00 | (2006.01) |
| B32B 5/24 | (2006.01) |
| B32B 29/02 | (2006.01) |
| B32B 27/12 | (2006.01) |
| B32B 37/12 | (2006.01) |
| B32B 27/08 | (2006.01) |
| B32B 27/30 | (2006.01) |
| B32B 27/36 | (2006.01) |
| B32B 43/00 | (2006.01) |
| B32B 5/02 | (2006.01) |
| B32B 27/10 | (2006.01) |
| B32B 27/00 | (2006.01) |
| B32B 5/26 | (2006.01) |
| B32B 27/06 | (2006.01) |
| B32B 37/26 | (2006.01) |

(52) U.S. Cl.
CPC ............ *B32B 7/12* (2013.01); *B32B 27/00* (2013.01); *B32B 27/06* (2013.01); *B32B 27/08* (2013.01); *B32B 27/10* (2013.01); *B32B 27/12* (2013.01); *B32B 27/306* (2013.01); *B32B 27/32* (2013.01); *B32B 27/36* (2013.01); *B32B 29/002* (2013.01); *B32B 29/005* (2013.01); *B32B 29/02* (2013.01); *B32B 37/12* (2013.01); *B32B 37/26* (2013.01); *B32B 43/006* (2013.01); *G01N 19/04* (2013.01); *B32B 2037/268* (2013.01); *B32B 2307/306* (2013.01); *B32B 2307/748* (2013.01); *B32B 2405/00* (2013.01); *G01N 2203/0091* (2013.01)

(58) Field of Classification Search
CPC . B32B 43/006; B32B 2037/268; B32B 5/022; B32B 5/24; B32B 5/26; B32B 27/08; B32B 27/10; B32B 27/12; B32B 27/306; B32B 27/32; B32B 27/36; B32B 29/002; B32B 29/005; B32B 29/02; B32B 2307/306; B32B 2405/00; G01N 19/04; G01N 2203/0091
USPC .................................................... 73/105 A
See application file for complete search history.

(56) References Cited

U.S. PATENT DOCUMENTS

| | | | |
|---|---|---|---|
| 2015/0147510 A1 | 5/2015 | Saito | |
| 2015/0344747 A1* | 12/2015 | Park | B32B 7/12 428/41.5 |
| 2018/0266114 A1* | 9/2018 | Tang | E04D 5/06 |

FOREIGN PATENT DOCUMENTS

| | | |
|---|---|---|
| JP | H01301781 A | 12/1989 |
| JP | 2013091785 A | 5/2013 |
| JP | 2014025047 A | 2/2014 |
| KR | 20130078388 A | 7/2013 |
| KR | 20130094748 A | 8/2013 |
| KR | 20140033680 A | 3/2014 |
| KR | 20140046590 A | 4/2014 |
| TW | 201321456 A | 6/2013 |
| TW | 201335584 A | 9/2013 |

OTHER PUBLICATIONS

Taiwanese Search Report for Application No. TW104135352 dated Jul. 12, 2018.
Chinese Search Report for Application No. 201580058061.6, dated Aug. 20, 2019, pp. 1-2.

* cited by examiner

[Figure 1]
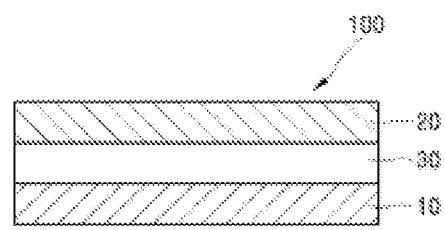
[Figure 2]
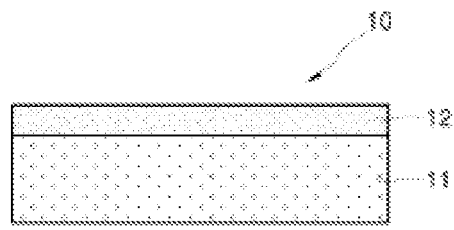

METHOD FOR MEASURING PEELING STABILITY OF RELEASE FILM AND RELEASE FILM LAMINATE

CROSS-REFERENCE TO RELATED APPLICATIONS

The present application is a national phase entry under 35 U.S.C. § 371 of International Application No. PCT/KR2015/011340 filed Oct. 26, 2015, which claims priority to Korean Application No. 10-2014-0147318 filed on Oct. 28, 2014, all of which are incorporated herein by reference.

TECHNICAL FIELD

The present invention relates to a method for measuring the peeling stability of a release film and a release film laminate.

BACKGROUND ART

A release film is a film which facilitates handling and transport of a product and can be easily separated, and has been utilized for various uses. For example, the release film may be used as a carrier film for an adhesive film. In this case, when a plurality of release films is used, there may occur a phenomenon in that an adhesive is lifted up or a problem in that an adhesive is transferred to the release film, depending on each difference in release strength. Therefore, there is a need for a verification means for selecting a release film having peeling stability in which a phenomenon in which an adhesive is lifted up does not occur because release strengths among a plurality of release films are balanced as a carrier for an adhesive film.

DETAILED DESCRIPTION OF THE INVENTION

Technical Problem

An exemplary embodiment of the present invention provides a method for measuring the peeling stability of a release film having high reliability and accuracy.

Another exemplary embodiment of the present invention provides a laminate including a release film which has excellent peeling stability measured by the method for measuring the peeling stability of the release film.

Technical Solution

An exemplary embodiment of the present invention provides a method for measuring the peeling stability of a release film, the method including the steps of: preparing a laminate including an adhesive layer and a light-peel release film and a medium-peel release film attached to both sides of the adhesive layer; obtaining a light-peel, low-speed release strength by measuring the release strength of the light-peel release film and the adhesive layer at the peeling speed of about 0.3 to about 3.0 m/min; obtaining a medium-peel, low-speed release strength by measuring the release strength of the medium-peel release film and the adhesive layer at the peeling speed of about 0.3 to about 3.0 m/min; obtaining a light-peel, high-speed release strength by measuring the release strength of the light-peel release film and the adhesive layer at the peeling speed of about 10 to about 30 m/min; obtaining a medium-peel, high-speed release strength by measuring the release strength of the medium-peel release film and the adhesive layer at the peeling speed of about 10 to about 30 m/min; and measuring a high-speed release strength balance and a low-speed release strength balance on the basis of the following General Formulas 1 and 2.

High-speed release strength balance=medium-peel, high-speed release strength/light-peel, high-speed release strength  [General Formula 1]

Low-speed release strength balance=medium-peel, low-speed release strength/light-peel, low-speed release strength  [General Formula 2]

The method for measuring the peeling stability of a release film may further include the steps of: measuring a light-peel speed change rate on the basis of the following General Formula 3 by using the light-peel, high-speed release strength and the light-peel, low-speed release strength; and measuring a medium-peel speed change rate on the basis of the following General Formula 4 by using the medium-peel, high-speed release strength and the medium-peel, low-speed release strength.

Light-peel speed change rate (%)=(light-peel, high-speed release strength−light-peel, low-speed release strength)/light-peel, low-speed release strength×100  [General Formula 3]

Medium-peel speed change rate (%)=(medium-peel, high-speed release strength medium-peel, low-speed release strength)/medium-peel, low-speed release strength×100  [General Formula 4]

The preparing of the laminate may include the step of storing the laminate at about 20° C. to about 100° C. for about 0.5 hour to about 720 hours.

The light-peel release film and the medium-peel release film may each include a laminated structure of a release layer and a base layer.

The release layer may include at least one selected from the group consisting of a silicone-based release agent, a melamine-based release agent, a polyolefin-based release agent, an epoxy-based release agent, an acrylic release agent, a fluorine-based release agent, a cellulose-based release agent, a paraffin-based release agent, an epoxy-melamine-based release agent, and a combination thereof.

The base layer may include at least one selected from the group consisting of polyethylene terephthalate (PET), polyethylene (PE), polyvinyl alcohol (PVA), and a combination thereof.

The adhesive layer may include at least one selected from the group consisting of an acrylic adhesive, a silicone-based adhesive, a rubber-based adhesive, and a combination thereof.

Another exemplary embodiment of the present invention provides a laminate including: an adhesive layer; and a light-peel release film and a medium-peel release film attached on both sides of the adhesive layer, in which both a high-speed release strength balance and a low-speed release strength balance measured by the method for the measuring the peeling stability of a release film are about 1.5 to about 5.0.

In the laminate, a light-peel speed change rate of the light-peel release film may be about 100% to about 300%, and a medium-peel speed change rate of the medium-peel release film may be about 200% to about 400%.

In the laminate, a light-peel, low-speed release strength of the light-peel release film may be about 10 to about 50 gf/50 mm, and a medium-peel, low-speed release strength of the medium-peel release film may be about 50 to about 200 gf/50 mm.

In the laminate, a light-peel, high-speed release strength of the light-peel release film may be about 10 to about 100 gf/50 mm, and a medium-peel, high-speed release strength of the medium-peel release film may be about 50 to about 200 gf/50 mm.

Advantageous Effects

In determining whether the peeling stability among a plurality of release films is excellent via the method for measuring the peeling stability of a release film, the efficiency may be secured, and a result having high reliability and accuracy may be obtained.

A laminate, which includes a release film having excellent peeling stability measured by the method for measuring the peeling stability of a release film, has physical properties suitable as a carrier for an adhesive film, and may reduce a defect rate when the adhesive film is applied to a target article.

BRIEF DESCRIPTION OF DRAWINGS

FIG. 1 schematically illustrates the cross-section of a laminate according to an exemplary embodiment of the present invention.

FIG. 2 schematically illustrates the cross-section of a light-peel release film.

BEST MODE

The benefits and features of the present invention, and the methods of achieving the benefits and features will become apparent with reference to Examples to be described below. However, the present invention is not limited to the Examples to be disclosed below, but may be implemented in various other forms, and the present Examples are only provided for rendering the disclosure of the present invention complete and for fully representing the scope of the invention to a person with ordinary skill in the technical field to which the present invention pertains, and the present invention will be defined only by the scope of the claims. Throughout the specification, like reference numerals indicate like constituent elements.

Method for Measuring Peeling Stability of Release Film

An exemplary embodiment of the present invention provides a method for measuring the peeling stability of a release film, the method including the steps of: preparing a laminate including an adhesive layer and a light-peel release film and a medium-peel release film attached to both sides of the adhesive layer; obtaining a light-peel, low-speed release strength by measuring the release strength of the light-peel release film and the adhesive layer at the peeling speed of about 0.3 to about 3.0 m/min; obtaining a medium-peel, low-speed release strength by measuring the release strength of the medium-peel release film and the adhesive layer at the peeling speed of about 0.3 to about 3.0 m/min; obtaining a light-peel, high-speed release strength by measuring the release strength of the light-peel release film and the adhesive layer at the peeling speed of about 10 to about 30 m/min; obtaining a medium-peel, high-speed release strength by measuring the release strength of the medium-peel release film and the adhesive layer at the peeling speed of about 10 to about 30 m/min; and measuring a high-speed release strength balance and a low-speed release strength balance on the basis of the following General Formulas 1 and 2.

High-speed release strength balance=medium-peel, high-speed release strength/light-peel, high-speed release strength [General Formula 1]

Low-speed release strength balance=medium-peel, low-speed release strength/light-peel, low-speed release strength [General Formula 2]

In general, a release film is used as a carrier for an adhesive layer of an adhesive film, and two release films having different release strengths are attached to both sides of the adhesive layer and may be distributed and transported. In this case, the lifting phenomenon of the adhesive layer may be prevented only when the two release films satisfy an appropriate release strength balance.

In order to determine whether the plurality of release films satisfies an appropriate release strength balance for one adhesive layer, the method for measuring the peeling stability of a release film may measure the peeling stability for a laminate by preparing the laminate including an adhesive layer and a light-peel release film and a medium-peel release film attached to both sides of the adhesive layer.

FIG. 1 schematically illustrates the cross-section of a laminate 100. The laminate 100 has a structure in which a light-peel release film 10, an adhesive layer 30, and a medium-peel release film 20 are sequentially laminated, and the light-peel release film 10 and the medium-peel release film 20 have different release strengths for the adhesive layer 30.

Specifically, the light-peel release film 10 has a lower release strength for the adhesive layer 30 than the medium-peel release film 20, and exhibits excellent peeling stability when the two release films have an appropriate release strength balance.

The method for measuring the peeling stability of a release film may include the step of obtaining a low-speed release strength for the light-peel release film and the medium-peel release film.

Specifically, the measurement method may include the steps of: obtaining a light-peel, low-speed release strength by measuring the release strength of the light-peel release film and the adhesive layer at the peeling speed of about 0.3 to about 3.0 m/min; and obtaining a medium-peel, low-speed release strength by measuring the release strength of the medium-peel release film and the adhesive layer at the peeling speed of about 0.3 to about 3.0 m/min.

The low-speed release strength of the light-peel release film and the medium-peel release film may be each measured at the peeling speed of about 0.3 to about 3.0 m/min, and may be measured specifically at the peeling speed of about 0.3 to about 1.0 m/min. When the low-speed release strength of each release film is measured at a peeling speed within the speed range, and accordingly, the release film is substantially manufactured into a product, it is possible to obtain a result in which reliability and accuracy are secured for the peeling stability of the release film.

Further, the method for measuring the peeling stability of a release film may include the step of obtaining a high-speed release strength for the light-peel release film and the medium-peel release film.

Specifically, the measurement method may include the steps of: obtaining a light-peel, high-speed release strength by measuring the release strength of the light-peel release film and the adhesive layer at the peeling speed of about 10 to about 30 m/min; and obtaining a medium-peel, high-speed release strength by measuring the release strength of the medium-peel release film and the adhesive layer at the peeling speed of about 10 to about 30 m/min.

The high-speed release strength of the light-peel release film and the medium-peel release film may be each measured at the peeling speed of about 10 to about 30 m/min, and may be measured specifically at the peeling speed of about 20 to about 30 m/min. When the high-speed release strength of each release film is measured at a peeling speed within the speed range, and accordingly, the release film is substantially manufactured into a product, it is possible to obtain a result in which reliability and accuracy are secured for the peeling stability of the release film.

The method for measuring the peeling stability of a release film includes the step of obtaining both a low-speed release strength and a high-speed release strength for each release film, and may include the step of measuring both a high-speed release strength balance and a low-speed release strength balance on the basis of General Formulas 1 and 2.

Since the measurement method measures both the high-speed release strength balance and the low-speed release strength balance, it is possible to secure a result having substantially high reliability and accuracy when release film is applied to and used for an actual product.

The method for measuring the peeling stability of a release film may further include the steps of: measuring a light-peel speed change rate on the basis of the following General Formula 3 by using the light-peel, high-speed release strength and the light-peel, low-speed release strength; and measuring a medium-peel speed change rate on the basis of the following General Formula 4 by using the medium-peel, high-speed release strength and the medium-peel, low-speed release strength.

Light-peel speed change rate (%)=(light-peel, high-speed release strength−light-peel, low-speed release strength)/light-peel, low-speed release strength×100  [General Formula 3]

Medium-peel speed change rate (%)=(medium-peel, high-speed release strength medium-peel, low-speed release strength)/medium-peel, low-speed release strength×100  [General Formula 4]

The measurement method may obtain more detailed and accurate information for the release strength balance of the light-peel release film and the medium-peel release film by further including the step of measuring the speed change rate on the basis of General Formulas 3 and 4, and may be advantageous in that the peeling stability of a release film may be more reliable, and a more accurate result may be secured.

In the method for measuring the peeling stability of a release film, the preparing of the laminate may include the step of storing the laminate at about 20° C. to about 100° C. for about 0.5 hour to about 720 hours. It may be advantageous in that the laminate is stored under the conditions, thereby enhancing the reliability of the result of measuring the low-speed release strength and the high-speed release strength.

FIG. 2 schematically illustrates the cross-section of the light-peel release film 10.

Referring to FIGS. 1 and 2, the light-peel release film 10 may include a laminated structure of a base layer 11 and a release layer 12. In this case, the laminate 100 may be a laminate in which the release layer 12 of the light-peel release film is attached to one side of the adhesive layer 30.

The release layer 12 may include at least one selected from the group consisting of specifically a silicone-based release agent, a melamine-based release agent, a polyolefin-based release agent, an epoxy-based release agent, an acrylic release agent, a fluorine-based release agent, a cellulose-based release agent, a paraffin-based release agent, an epoxy-melamine-based release agent, and a combination thereof.

The medium-peel release film 20 may have the same laminated structure as that of the light-peel release film 10. That is, the medium-peel release film 20 may also include a laminated structure of a base layer and a release layer, and in this case, the laminate 100 may be a laminate in which the release layer of the medium-peel release film is attached to the side opposite to the one side to which the release layer 12 of the light-peel release film is attached.

For example, the release layer of the light-peel release film and the release layer of the medium-peel release film may each include a silicone-based release agent. In this case, it may be advantageous in that a result obtained by the method for measuring the peeling stability of a release film secures high reliability and accuracy.

In addition, the base layer of the light-peel release film and the base layer of the medium-peel release film may each include at least one selected from the group consisting of paper, a non-woven fabric, polyethylene terephthalate (PET), polyethylene (PE), polyvinyl alcohol (PVA), and a combination thereof. For example, the base layer of the light-peel release film and the base layer of the medium-peel release film may include polyethylene terephthalate (PET) or polyethylene (PE), and in this case, both the base layers have excellent heat resistance, and accordingly, it is possible to obtain a result having high accuracy and reliability via the method for measuring the peeling stability of a release film.

An adhesive layer, which may be transported or distributed by using the release film, may include at least one selected from the group consisting of specifically an acrylic adhesive, a silicone-based adhesive, a rubber-based adhesive, and a combination thereof, but is not limited thereto.

For example, the adhesive layer may include an acrylic adhesive, and in this case, it may be advantageous in that an accurate result for the peeling stability may be obtained by the method for measuring the peeling stability of a release film.

Laminate

An exemplary embodiment provides a laminate including: an adhesive layer; and a light-peel release film and a medium-peel release film attached on both sides of the adhesive layer, in which both a high-speed release strength balance and a low-speed release strength balance measured by the method for measuring the peeling stability of a release film are about 1.5 to about 5.0.

Both the high-speed release strength balance and the low-speed release strength balance may be about 1.5 to about 5.0, and may be specifically about 1.7 to about 3.0. When both the high-speed release strength balance and the low-speed release strength balance satisfy the range, the release films of the laminate may implement excellent peeling stability, and when only the light-peel release film is removed, the adhesive layer is not peeled off from the medium-peel release film, and it is possible to prevent a problem in that the adhesive layer is lifted up, or the adhesive is transferred to the release film.

Furthermore, the light-peel speed change rate of the light-peel release film may be about 300% or less, and may be, for example, about 100% to about 300%. Further, the medium-peel speed change rate of the medium-peel release film may be 200% or more, and may be, for example, about 200% to about 400%. The light-peel speed change rate and the medium-peel speed change rate may be obtained by using General Formulas 3 and 4.

When the light-peel release film and the medium-peel release film satisfy a high-speed release strength balance and a low-speed release strength balance within the range, and simultaneously, exhibit a light-peel speed change rate and a medium-peel speed change rate within the range, the release films of the laminate may secure excellent peeling stability without a phenomenon in which the adhesive layer is lifted up or transferred.

Specifically, the light-peel, low-speed release strength of the light-peel release film may be about 10 to about 50 gf/50 mm, and the medium-peel, low-speed release strength of the medium-peel release film may be about 50 to about 200 gf/50 mm. That is, the release strengths, which are measured at the peeling speed of about 0.3 to about 3.0 m/min for the light-peel release film and the medium-peel release film, may each satisfy the range. When the light-peel, low-speed release strength and the medium-peel, low-speed release strength satisfy the range, the light-peel release film is easily peeled off by a predetermined force without causing a problem in that the light-peel release film is spontaneously peeled off, and when only the light-peel release film is peeled off, it is possible to prevent a problem in that the adhesive layer is lifted up because the medium-peel release film is firmly bonded to the adhesive layer.

In addition, the light-peel, high-speed release strength of the light-peel release film may be about 10 to about 100 gf/50 mm, and the medium-peel, high-speed release strength of the medium-peel release film may be about 50 to about 200 gf/50 mm. That is, the release strengths, which are measured at the peeling speed of about 10 to about 30 m/min for the light-peel release film and the medium-peel release film, may each satisfy the range. When the light-peel, high-speed release strength and the medium-peel, high-speed release strength satisfy the range, the light-peel release film is easily peeled off by a predetermined force without causing a problem in that the light-peel release film is spontaneously peeled off, and when only the light-peel release film is peeled off, it is possible to prevent a problem in that the adhesive layer is lifted up because the medium-peel release film is firmly bonded to the adhesive layer.

Hereinafter, specific examples of the present invention will be suggested. However, the Examples described below are only provided for specifically exemplifying or explaining the present invention, and the present invention is not limited thereby.

Example 1

A laminate including an acrylic adhesive layer and a light-peel release film and a medium-peel release film attached to both sides of the adhesive layer was prepared. The component and content of each release layer and base layer of the light-peel release film and the medium-peel release film are shown in the following Table 1. Subsequently, for the light-peel release film and the medium-peel release film, a light-peel, low-speed release strength (A) and a medium-peel, low-speed release strength (B) were measured by measuring the release strength at the peeling speed of 0.3 m/min. Subsequently, for the same laminate, a light-peel, high-speed release strength (C) and a medium-peel, high-speed release strength (D) were measured by measuring the release strength at the peeling speed of 30 m/min. Subsequently, a low-speed release strength balance and a high-speed release strength balance were measured by calculating the values of B/A and D/C. Furthermore, a light-peel speed change rate (%) was measured by using the equation of (C−A)/A×100, and a medium-peel speed change rate (%) was measured by using the equation of (D−B)/B× 100. The results are shown in the following Table 3.

TABLE 1

|  |  | Polydimethylsiloxane (PDMS) | Silicone resin | Pt-based catalyst |
| --- | --- | --- | --- | --- |
| Light-peel release film | Release layer | To 100 | — | 5 |
|  | Base layer | 100 μm PET film | | |
| Medium-peel release film | Release layer | To 100 | 20 | 5 |
|  | Base layer | 100 μm PET film | | |

Example 2

The component and content of each release layer and base layer of the light-peel release film and the medium-peel release film are shown in the following Table 2, and except for the component and content, the low-speed release strength balance, the high-speed release strength balance, the light-peel speed change rate, and the medium-peel speed change rate were measured in the same manner as in Example 1. The results are shown in the following Table 3.

TABLE 2

|  |  | Polydimethylsiloxane (PDMS) | Silicone resin | Pt-based catalyst |
| --- | --- | --- | --- | --- |
| Light-peel release film | Release layer | To 100 | — | 5 |
|  | Base layer | 100 μm PET film | | |
| Medium-peel release film | Release layer | To 100 | 30 | 5 |
|  | Base layer | 100 μm PET film | | |

The low-speed release strength balance, the high-speed release strength balance, the light-peel speed change rate, and the medium-peel speed change rate, which were measured by the method for measuring the peeling stability of a release film in Examples 1 and 2, are shown in the following Table 3.

TABLE 3

|  | Low-speed release strength balance | High-speed release strength balance | Light-peel speed change rate (%) | Medium-peel speed change rate (%) |
| --- | --- | --- | --- | --- |
| Example 1 | 2.5 | 2.0 | 150 | 250 |
| Example 2 | 2.8 | 1.0 | 180 | 100 |

In Examples 1 and 2, the peeling stability was measured by the method for measuring the peeling stability of a release film, and referring to the results in Table 3, it can be seen that Example 1 exhibits excellent peeling stability because both the low-speed release strength balance and the high-speed release strength balance satisfy the range from 1.5 to 5.0.

In contrast, in Example 2, as a result of measuring the peeling stability by the method for measuring the peeling stability of a release film, it can be seen that the low-speed release strength balance satisfies the range from 1.5 to 5.0, but the high-speed release strength balance value is 1.0, and the peeling stability was poor because the low-speed release strength balance and the high-speed release strength balance do not both satisfy the range from 1.5 to 5.0.

Further, in Example 1, the light-peel speed change rate was 300% or less, the medium-peel speed change rate was 200% or more, and it can be seen that the release films of the laminate secure excellent peeling stability without a phenomenon in which the release film of the laminate is lifted up or transferred by satisfying a high-speed release strength balance and a low-speed release strength balance within the ranges, and simultaneously, exhibiting a light-peel speed change rate within the range and a medium-peel speed change rate within the range.

In contrast, in Example 2, the light-peel speed change rate was 300% or less, but the medium-peel speed change rate was less than 200%, and accordingly, it can be seen that the peeling stability is poor as compared to Example 1.

EXPLANATION OF REFERENCE NUMERALS AND SYMBOLS

100: Laminate
10: Light-peel release film
20: Medium-peel release film
30: Adhesive layer
11: Base layer
12: Release layer

The invention claimed is:

1. A method for measuring the peeling stability of a release film, the method including the steps of:
    preparing a laminate including an adhesive layer and a light-peel release film and a medium-peel release film attached to both sides of the adhesive layer;
    obtaining a light-peel, low-speed release strength by measuring the release strength of the light-peel release film and the adhesive layer at the peeling speed of 0.3 to 3.0 m/min;
    obtaining a medium-peel, low-speed release strength by measuring the release strength of the medium-peel release film and the adhesive layer at the peeling speed of 0.3 to 3.0 m/min;
    obtaining a light-peel, high-speed release strength by measuring the release strength of the light-peel release film and the adhesive layer at the peeling speed of 10 to 30 m/min;
    obtaining a medium-peel, high-speed release strength by measuring the release strength of the medium-peel release film and the adhesive layer at the peeling speed of 10 to 30 m/min; and
    measuring a high-speed release strength balance and a low-speed release strength balance on the basis of the following General Formulas 1 and 2

$$\text{High-speed release strength balance} = \frac{\text{medium-peel, high-speed release strength}}{\text{light-peel, high-speed release strength}} \quad \text{[General Formula 1]}$$

$$\text{Low-speed release strength balance} = \frac{\text{medium-peel, high-speed release strength}}{\text{light-peel, high-speed release strength}} \quad \text{[General Formula 2]}$$

2. The method of claim 1, further comprising the steps of:
    measuring a light-peel speed change rate on the basis of the following General Formula 3 by using the light-peel, high-speed release strength and the light-peel, low-speed release strength; and
    measuring a medium-peel speed change rate on the basis of the following General Formula 4 by using the medium-peel, high-speed release strength and the medium-peel, low-speed release strength;

$$\text{Light-peel speed change rate (\%)} = \frac{(\text{light-peel, high-speed release strength} - \text{light-peel, low-speed release strength})}{\text{light-peel, low-speed release strength} \times 100} \quad \text{[General Formula 3]}$$

$$\text{Medium-peel speed change rate (\%)} = \frac{(\text{medium-peel, high-speed release strength} - \text{medium-peel, low-speed release strength})}{\text{medium-peel, low-speed release strength} \times 100} \quad \text{[General Formula 4]}$$

3. The method of claim 1, wherein the preparing of the laminate comprises the step of storing the laminate at 20° C. to 100° C. for 0.5 hour to 720 hours.

4. The method of claim 1, wherein the light-peel release film and the medium-peel release film each comprise a laminated structure of a release layer and a base layer.

5. The method of claim 4, wherein the release layer comprises at least one selected from the group consisting of a silicone-based release agent, a melamine-based release agent, a polyolefin-based release agent, an epoxy-based release agent, an acrylic release agent, a fluorine-based release agent, a cellulose-based release agent, a paraffin-based release agent, an epoxy-melamine-based release agent, and a combination thereof.

6. The method of claim 4, wherein the base layer comprises at least one selected from the group consisting of polyethylene terephthalate (PET), polyethylene (PE), polyvinyl alcohol (PVA), and a combination thereof.

7. The method of claim 1, wherein the adhesive layer comprises at least one selected from the group consisting of an acrylic adhesive, a silicone-based adhesive, a rubber-based adhesive, and a combination thereof.

* * * * *